(12) United States Patent
Fuchs

(10) Patent No.: US 6,235,905 B1
(45) Date of Patent: May 22, 2001

(54) PROCESS FOR PREPARING ALKOXYPYRAZINE DERIVATIVES

(75) Inventor: Rudolf Fuchs, Sion (CH)

(73) Assignee: Lonza AG, Gampel/Valais (CH)

( * ) Notice: Subject to any disclaimer, the term of this patent is extended or adjusted under 35 U.S.C. 154(b) by 0 days.

(21) Appl. No.: 09/583,096

(22) Filed: Jan. 28, 2000

Related U.S. Application Data

(62) Division of application No. 09/105,987, filed on Jun. 29, 1998, now Pat. No. 6,066,736.

(30) Foreign Application Priority Data

Jul. 3, 1997 (CH) .................................................. 1615/97

(51) Int. Cl.[7] .................................................. C07D 241/14
(52) U.S. Cl. .......................................... 544/406; 544/408
(58) Field of Search ...................... 544/406, 408

(56) References Cited

U.S. PATENT DOCUMENTS

| 3,660,400 | 5/1972 | Cragoe et al. | 544/406 |
| 3,745,161 | 7/1973 | Shen et al. | 544/406 |
| 4,041,032 | 8/1977 | Murakami et al. | 544/407 |

FOREIGN PATENT DOCUMENTS

| 1366718 | 7/1960 | (FR) . |
| 922735 | 4/1963 | (GB) . |
| 1269484 | 4/1972 | (GB) . |

OTHER PUBLICATIONS

M. Botta et al., J. of Heterocyclic Chemistry, vol. 16, (1979), pp. 193–194.

*Chemical Abstracts*, vol. 88, No. 3, p. 644, col. 2, abstract 22972.

Hideki Hirano et al., J. of Heterocyclic Chemistry, vol. 19, (1982), pp. 1409–1413.

Katritzky, Comprehensive Het. Chem., vol. 3, (1984), pp. 179–197.

*Primary Examiner*—Michael G. Ambrose
(74) *Attorney, Agent, or Firm*—Fisher Christen & Sabol

(57) ABSTRACT

A process for preparing alkoxypyrazine derivatives of the general formula:

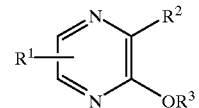

Ia

These alkoxypyrazine derivatives are obtained by reacting a glyoxal derivative of the general formula:

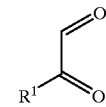

II and an amlinoimidate of the general formula:

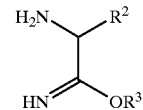

III

The alkoxypyrazine derivatives are important intermediates for preparing pharmaceutically active compounds.

8 Claims, No Drawings

PROCESS FOR PREPARING ALKOXYPYRAZINE DERIVATIVES

This application is a division of U.S. Ser. No. 09/105,987, filed on Jun. 29, 1998, now U.S. Pat. No. 6,066,736.

BACKGROUND OF THE INVENTION

1. Field of the Invention

The invention relates to a novel process for preparing alkoxypyrazine derivatives of the general formula:

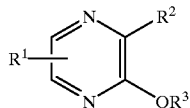

Ia in which $R^1$ denotes hydrogen, alkyl or aryl, $R^2$ denotes hydrogen, alkyl, —$CONH_2$, —$COOR^4$, in which $R^4$ denotes alkyl, or —$C(NH)OR^4$, in which $R^4$ is as defined above, and $R^3$ denotes alkyl or aryl. Moreover, the invention relates to a novel process for preparing alkoxypyrazineamine derivatives of the general formula:

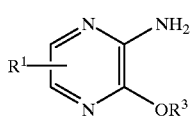

Va in which $R^1$ and $R^3$ are as defined above.

2. Background Art

Both the alkoxypyrazine derivatives of the general formula Ia and the alkoxypyrazineamine derivatives of the general formula V are important intermediates for preparing pharmaceutically active compounds [*Katritzky* Comprehensive Het. Chem., Vol. 3, (1984), 179–197].

A number of processes for preparing pyrazine derivatives are known from the above-mentioned literature reference.

British Published Patent Application No. 922,725, for example, describes a process for preparing 3-methoxy-5-methylpyrazine-2-amine by reaction of 3-chloro-5-methylpyrazine-2-amine with sodium methoxide.

BROAD DESCRIPTION OF THE INVENTION

It is an object of the present invention to provide a novel alternative access to alkoxypyrazine and alkoxypyrazineamine derivatives. This object is successfully achieved by the novel process according to the invention.

The key step of the synthesis according to the invention according to the first process of the invention is the reaction of a glyoxal derivative of the general formula:

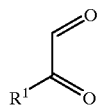

II in which $R^1$ is as defined above with an aminoimidate of the general formula:

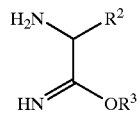

III in which $R^2$ and $R^3$ are as defined above to give the alkoxypyrazine derivative of the general formula:

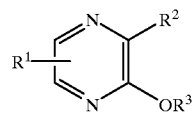

Ia in which $R^1$ denotes hydrogen, alkyl or aryl, $R^2$ denotes hydrogen, alkyl, —$CONH_2$, —$COOR^4$, in which $R^4$ denotes alkyl, or —$C(NH)OR^4$, in which $R^4$ is as defined above, and $R^3$ denotes alkyl or aryl.

The radicals $R^1$ to $R^5$ are as defined below:

Alkyl denotes a $C_1$–$C_6$-alkyl group, specifically methyl, ethyl, n-propyl, isopropyl, n-butyl, isobutyl, t-butyl, pentyl and its isomers and hexyl and its isomers.

Alkyl preferably denotes a $C_1$–$C_4$-alkyl group. The alkyl group can optionally be substituted by one of the alkyl groups mentioned, by aryl, by a halogen, by an alkoxy group, by an amino, by an alkylamino or by a dialkylamino group.

For the purpose of the invention, aryl is to be understood as an optionally substituted phenyl or naphthyl group. Suitable substituents are the above-mentioned alkyl groups, halogen, alkoxy, amino, alkylamino or dialkylamino.

The preferred aryl group is phenyl. The preferred aryl-substituted alkyl group is benzyl. For the purpose of the invention, halogen denotes fluorine, chlorine, bromine or iodine, preferably chlorine.

Depending on the substitution pattern of the reactants, the group $R^1$ can be positioned regioselectively in position 5 or position 6 of the alkoxypyrazine derivative.

Generally and also preferably, an alkoxypyrazine derivative of the general formula:

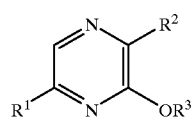

Ib results in which $R^1$ is in position 5.

The glyoxal derivatives of the general formula II are generally available commercially. This is true in particular for the preferably used compounds glyoxal ($R^1$==H), methylglyoxal ($R^1$=$CH_3$) and phenylglyoxal ($R^1$=phenyl). However, it is also possible to employ other glyoxal compounds of the general formula II where $R^1$=t-butyl or haloalkyl, such as, for example, di- or triflhalomethyl, in particular di- or trifluoromethyl or di-trichloromethyl.

The aminoimidate of the general formula III used as reaction partner of the glyoxal derivative of the general formula II is a compound whose presence can be reaffirmed unambiguously, but which can usually not be isolated in stable form. According to one subembodiment of the invention, the aminoimidate of the general formula III is therefor advantageously prepared by reacting an aminonitrile of the general formula:

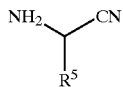

IV in which $R^5$ has the meaning of $R^2$ or of cyano, with an alkali metal alkoxide or alkaline earth metal alkoxide and then reacted further, directly and without isolation, with the glyoxal derivative of the general formula II to give the alkoxypyrazine derivative of the general formula Ia.

The reaction is advantageously carried out by initially charging the amino nitrile of the general formula IV in a suitable solvent, preferably in an aliphatic alcohol, followed by reaction with the alkali metal alkoxide or alkaline earth metal alkoxide in question at a temperature of advantageously –30° C. to 150° C.

Preference is given to using alkali metal alkoxides, such as sodium methoxide or potassium methoxide or sodium ethoxide or potassium ethoxide.

Depending on the group $R^2$ in the resulting aminoimidate of the general formula III, it may be advantageous to neutralize the reaction mixture with a suitable acid beforehand.

Suitable acids are simple carboxylic acids, such as acetic acid, or mineral acids, such as, sulfuric acid or hydrochloric acid.

The aminoimidate of the general formula III can usually not be isolated in stable form, but its presence can be reaffirmed unambiguously by spectroscopic methods such as $^{13}C$ NMR. Consequently, further reaction with the glyoxal derivative usually follows. This is advantageously carried out at a temperature of –30° C. to 150° C., preferably of –10° C. to 10° C.

The glyoxal derivative of the general formula II is usually employed in a slight excess, based on the aminonitrile of the general formula IV.

The reaction has usually ended after 0.1 hour to 40 hours, and the alkoxypyrazine of the general formula I can then be isolated in a customary manner, for example by extraction from the reaction mixture.

Alkoxypyrazine derivatives of the general formula Ia where $R^1$ and $R^3$ denote alkyl or aryl and $R^2$ denotes —$CONH_2$, $COOR^4$, where $R^4$ denotes alkyl, or —C(NH)$OR^4$, where $R^4$ is as defined above, are novel and not known from the literature and are therefore also part of the subject-matter of the present invention. Specifically, such novel alkoxypyrazine derivatives are:

3-methoxy-5-methylpyrazine-2-carboxamide;
3-ethoxy-5-methylpyrazine-2-carboxamide;
methyl 3-methoxy-5-methylpyrazine-2-carboxylate;
methyl 3-ethoxy-5-methylpyrazine-2-carboxylate;
3-methoxy-5-phenylpyrazine-2-carboxamide;
3-ethoxy-5-phenylpyrazine-2-carboxamide;
methyl 3-methoxy-5-methylpyrazine-2-inimidocarboxylate;
methyl 3-ethoxy-5-methylpyrazine-2-imidocaroxylate;
ethyl 3-methoxy-5-methylpyrazine-2coxylate; and
ethyl 3-ethoxy-5-methylpyrazine-2-carboxylate.

The reaction according to the invention is preferably suitable for preparing 3-methoxy-5-methylpyrazine-2carboxamide (general formula Ib where $R^1$ denotes methyl, $R^2$ denotes —$CONH_2$, and $R^3$ denotes methyl). To this end, either 2-amino-2-cyanoacetamide (general formula IV where $R^1$ denotes —$CONH_2$) or 2-aminomalononitrile (general formula IV where $R^5$ denotes —CN), or a salt thereof, can be used as the starting material.

Starting from 2-amino-2-cyanoacetamide, the target compound is obtained by the above-described reaction with the alkali metal alkoxide or alkaline earth metal alkoxide and subsequent neutralization via the aminoimidate intermediate (general formula III where $R^2$ denotes —$CONH_2$ and $R^3$ denotes methyl) and after reaction with methylglyoxal (general formula II where $R^1$ denotes methyl).

Starting from 2-aminomalononitrile, or a salt thereof, the target compound is obtained by the above-described reaction with the alkali metal alkoxide or alkaline earth metal alkoxide and subsequent neutralization via the aminoimidate intermediate (general formula m where $R^2$ denotes —C(NH)$OCH_3$ and $R^3$ denotes methyl), after its reaction with methylglyoxal (general formula II where $R^1$ denotes methyl) via methyl 3-methoxy-5-methylpyrazine-2-imidocarboxylate, after its acidification to give methyl 3-methoxy-5-methylpyrazine-2-carboxylate and finally after its amidation.

In the last variant, methyl 3-methoxy-5-methylpyrazine-2-imidocarboxylate is not isolated but directly converted into the carboxylic ester mentioned by acidification of the reaction mixture. The acidification and the amidation is carried out in a known manner using a mineral acid and ammonia, respectively.

The alkoxypyrazine derivatives of the general formula Ia preparable according to the invention where $R^2$ denotes —$CONH_2$ and $R^1$ and $R^3$ are defined as above, can, according to a further aspect of the invention, be converted, according to the principles of the Hofmann degradation, into alkoxypyranneamine derivatives of the general formula:

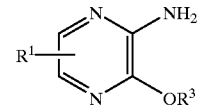

Va where $R^1$ and $R^3$ are as defined above, using an alkali metal hypohalite.

Preference is given to preparing, starting from the alkoxypyrazine derivatives of the general formula Ib, the alkoxypyrazineamine derivatives of the general formula:

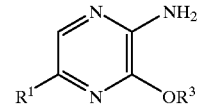

Vb in which $R^1$ and $R^3$ are as defined above.

The Hofmann degradation is known from the literature. The reaction is usually carried out using an alkali metal hypobromite solution, which is customarily prepared from the corresponding alkali metal hydroxide and bromine, at a reaction temperature between –20° C. and 100° C.

The alkoxypyrazineamine derivative can be isolated from the reaction mixture in a customary manner known to the person skilled in the art, for example, by extraction.

DETAILED DESCRIPTION OF THE INVENTION

Example 1

(a) Synthesis of methyl (2-amino-2-carbonyl) acetoimidate

Under argon, 1.09 g (10.3 mmol) of 2-amino-2-cyanoacetamide was initially charged in 11 g of methanol.

0.29 g (1.6 mmol) of sodium methoxide solution (30%) was added and the mixture was stirred at 20° C. for 2 hours. The structure of the title product was confirmed by NMR, with the data being:

$^1$H-NMR (DMSO-$d_6$, 400 MHz)δ: 3.85 (s, 3H);

4.18 (s, 1H);

8.2–8.6 (sb, 1H).

$^{13}$C-NMR (DMSO-$d_6$, 400 MHz)δ: 52.27 (q);

55.83 (d);

171.66 (s);

172.78 (s).

(b) Synthesis of 3-methoxy-5-methylpyrazine-2-carboxamide

Under argon, 6 g (60.5 mmol) of 2-amino-2cyanoacetamide was initially charged in 67 g of methanol. 1.67 g (9.3 mmol) of sodium methoxide solution (30%) was added and the mixture was stirred for at 20° C. 2 hours. After nuetralization with 0.558 g (9.3 mmol) of acetic acid, 11.55 g (64.1 mmol) of methylglyoxal solution (40%) was added. The mixture was stirred at 20° C. for 2 hours and then at 50° C. for 2 hours. The solvent was distilled off and the 3-methoxy-5-methylpyrazine-2-carboxamide was purified by column chromatography (eluent: ethyl acetate/methanol 4:1). This gave 5 g of 3-methoxy-5-methylpyrazine-2-carboxamide. The yield was 50 percent. Other data concerning the title product was: $^1$H-NMR (DMSO-$d_6$, 400 MHz) 5: 8.10 (s, 1H);

7.84 and 7.56 (2s, broad 2H);

3.93 (s, 3H);

2.46 (s, 3H).

$^{13}$C-NMR (DMSO-$d_6$, 400 MHz)δ: 165.5 (s);

156.6 (s);

152.4 (s);

134.5 (s);

134.3 (d);

53.4 (q);

20.7 (q).

(c) Synthesis of 3-methoxy-5-methylpyrazine-2-carboxamide

Under argon, 6 g (60.5 mmol) of 2-amino-2-cyanoacetamide was initially charged in 67 g of methanol. 1.67 g (9.3 mmol) of sodium methoxide solution (30%) was added and the mixture was stirred at 20° C. for 2 hours. At 0° C., 11.55 g (64.1 mmol) of methylglyoxal solution (40%) was added and the mixture was stirred at 0° C. for 2 hours. The solution was then cooled to −20° C. The product precipitated out. After filtration and drying, 3.56 g of the title product was obtained. The yield was 39 percent. The melting point of the title product was 170° C. to 172° C. Other data concerning the title product was: $^1$H-NMR (DMSO-$d_6$, 400 MHz)δ: 8.10 (s, 1H);

7.84 and 7.56 (2s broad, 2H);

3.93 (s, 3H);

2.46 (s, 3H).

$^{13}$C-NMR (DSMO-$d_6$, 400 MHz)δ: 165.5 (s);

156.6 (s);

152.4 (s);

134.5 (s);

134.3 (d);

53.4 (q);

20.7 (q).

Example 2

(a) Synthesis of 3-methoxy-5-methylpyrazine-2-amine 3.71 g (56.2 mmol) of potassium hydroxide (85%) and 31 g of water were initially charged in a flask. At 1° C., 2.16 g (13.5 mmol) of bromine was added dropwise over a period of 10 minutes. This potassium hypobromite solution was added dropwise at 4° C. to an aqueous solution of 2.27 g (13.1 mmol) of 3-methoxy-5-methylpyrazine-2-carboxamide in 12 g of water. The mixture was stirred at 1° C. for one hour and then at 98° C. for 3 hours. The resultant 3-methoxy-5-methylpyrazine-2-amine was extracted at 20° C. using methylene chloride (2 times 25 ml). Removal of the solvent gave 0.92 g of 3-methoxy-5-methylpyrazine-2-amine. The yield was 50.4 percent. The melting point of the title product was 75° C. to 76.5° C. The other data concerning the title product was: $^1$H-NMR (DMSO-$d_6$, 400 MHz)δ: 2.20 (s, 3H);

3.87 (s, 3H);

5.90 (s, 2H);

7.33 (s, 1H).

(b) Synthesis of 3-methoxy-5-methylpyrazine-2-amine 1.54 g (23.3 mmol) of potassium hydroxide (85%) and 15 g of water were initially charged in a flask. At 1° C., 1.08 g (5.53 mmol) of bromine was added dropwise over a period of 10 minutes. This potassium hypobromite solution was added dropwise at 4° C. to an aqueous solution of 1.04 g (5.76 mmol) of 3-methoxy-5-methylpyrazine-2-carboxamide in 6.5 g of water. The mixture was stirred at 1° C. for 1 hour and then at 83° C. for 3 hours. The 3-methoxy-5-methylpyrazine-2-amine was extracted at 20° C. using methylene chloride (2 times 15 ml). Removal of the solvent gave 0.65 g of the title product. The yield was 80 percent. The melting point of the title product was 75° C. to 76.5° C. Other data concerning the title product was:

$^1$H-NMR (DMSO-$d_6$, 400 MHz)δ: 2.20 (s, 3H);

3.87 (s, 3H);

5.90 (s, 2H);

7.33 (s, 1H).

Example 3

Synthesis of 3-methoxypyrazine-2-carboxamide

Under argon, 1 g (10.1 mmol) of 2-amnino-2-cyanoacetarmide was initially charged in 10 g of methanol. 0.25 g (1.4 mmol) of sodium methoxide solution (30%) was added and the mixture was stirred at 20° C. for 2 hours. After neutralization with 0.084 g (1.4 mmol) of acetic acid, 2.27 g (20 mmol) of glyoxal solution (40%) was added. The mixture was stirred at 20° C. for 2 hours and then at 50° C. for 2 hours. The solvent was distilled off. This gave 0.75 g of 3-methyoxypyrazine-2carboxamide. The yield was 50 percent. Other data concerning the title product was:

$^1$H-NMR (DMSO-$_6$, 400 MHz)δ: 3.18 (s, 3H);

3.95 (s, 3H);

7.63 (s, 1H);

7.93 (s, 1H);

8.22 (d, 1H, J=1Hz);

8.37 (d, 1H, J=1Hz).

Example 4

Synthesis of methyl 3-methoxy-5-methylpyrazine-2-carboxylate

Under argon, 5 g (19.3 mmol) of 2-aminomalononitrile-4-toluenesulfonate was initially charged in 50 g of methanol.

4.09 g (22.7 mmol) of sodium methoxide solution (30%) was added and the mixture was stirred at 2° C. for 2 hours. After neutralization with 0.204 g (3.4 mmol) of acetic acid, 3.6 g (19.9 mmol) of methylglyoxal solution (40%) was added. The mixture was stirred at 40° C. for 2 hours and then, at 20° C., 9.2 g (80 mmol) of hydrochloric acid (32%) was added and the mixture was stirred at 20° C. for 6 hours. The solvent was distilled off and the methyl 3-methoxy-5-methylpyrazine-2-carboxylate was extracted with methylene chloride. This gave 1 g of methyl 3-methoxy-5-methylpyrazine-2-carboxylate. The yield was 27 percent Other data concerning the title product was:

¹H-NMR (CDCl₃, 400 MHz)δ: 2.54 (s, 3H);
3.98 (s, 3H);
4.07 (s, 1H);
8.12 (s, 1H).
¹³C-NMR (CDCl₃, 400 MHz)δ: 21.4 (q);
52.7 (q);
54.2 (q);
129.7 (s);
135.4 (d);
155.4 (s);
158.9 (s);
164.3 (s).

Example 5

Synthesis of 3-methoxy-5-methylpyrazine-2-carboxamide 1 g (5.5 mmol) of methyl 3-methoxy-5-methylpyrazine-carboxylate was initially charged in 15 ml (198 mmol) of NH₃ (25%) and the mixture was stied at 50° C. After concentration, 0.8 g of 3-methoxy-5-methylpyrazine-2carboxamide was obtained. The yield was 86 percent. Other data concerning the title product was:

¹H-NMR (DMSO-d₆, 400 MHz)δ: 8.10 (s, 3H);
7.84 and 7.56 (2s broad, 2H);
3.93 (s, 3H);
2.46 (s, 3H).

Example 6

Synthesis of 3-methoxy-5-phenylpyrazine-2-carboxamide

Under argon, 2 g (20 mmol) of 2-amino-2-cyanoacetamide was initially charged in 15 g of methanol. 0.55 g (3 mmol) of sodium methoxide solution (30%) was added and the mixture was stirred at 20° C. for 2 hours. At 0° C., 3.2 g (21 mmol) of phenylglyoxal was added and the mixture was then stirred at 0° C. for 2 hours and concentrated. The product was purified by column chromatography (eluent ethyl acetate/methanol 4/1). This gave 3 g of 3-methoxy-5-phenylpyrazine-2-carboxamide. The yield was 65 percent. Other data concerning the title product was:

¹H-NMR (DMSO-d₆, 400 MHz)δ: 4.04 (s, 3H);
7.5–8.0 (m, 7H);
8.83 (s, 1H).
¹³C-NMR (DMSO-d₆, 400 MHz)δ: 53.45;
127;
128.7;
130.24;
131.7;
134.99;
135.90;
149.4;
156.66;
165.3.
MS: 229 (100%)

What is claimed is:

1. A process for preparing an alkoxypyrazine derivative of the formula:

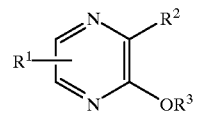

Ia in which R¹ denotes hydrogen, alkyl, —CONH₂, —COOR⁴, in which R⁴ is as defined above, and R³ denotes alkyl or aryl, comprising the formula:

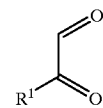

II in which R¹ is as defined above, with an aminoimidate of the formula:

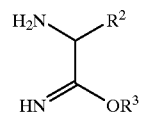

III in which R² and R³ are as defined above.

2. The process according to claim 1, wherein the aminoimidate of the formula III is prepared by reacting an aminonitrile of the formula:

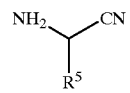

IV in which R¹ has the meaning of R² or of cyano, with an alkali metal alkoxide or alkaline earth metal alkoxide and is then reacted further, directly and without isolation, with the glyoxal derivative or the formula II to give the alkoxypyrazine derivative of the formula I.

3. The process according to claim 2 for preparing 3-methoxy-5-methylpyrazine-2-carboxamide, wherein 2-amino-2-cyanoacetimide is converted, using an alkali metal methoxide or alkaline earth metal methoxide and subsequently neutralization, into the aminoimidate of the formula III in which R² denotes —CONH₂ and R³ denotes methyl, and said aminoimidate is reacted, without isolation, with methylglyoxal.

4. The process according to claim 2 for preparing 3-methoxy-5-methylpyrazine-2-carboxamide, wherein 2-aminomalononitrile, or salt thereof, is converted, using an alkali metal methoxide or alkaline earth metal alkoxide and subsequent neutralization, into the aminoimidate of the formula III in which R² denotes —C(NH)OCH₃ and R³ denotes methyl, said aminoimidate is reacted, without isolation, with methylglyoxal and, after acidification, initially converted into methyl 3-methoxy-5-methylpyrazine-2-carboxylate, and the ester function is finally amidated.

5. The process according to claim 4, wherein the reaction with an alkali metal methoxide or alkaline earth metal alkoxide and the reaction with the glyoxal derivative is carried out at a temperature of between −30° C. and 150° C.

6. The process according to claim 1 for preparing 3-methoxy-5-methylpyrazine-2-carboxamide, wherein 2-amino-2-cyanoacetamide is converted, using an alkali metal methoxide or alkaline earth metal methoxide and subsequently neutralization, into the aminoimidate of the formula III in which $R^2$ denotes —$CONH_2$ and $R^3$ denotes methyl and said aminoimidate is reacted, without isolation, with methylglyoxal.

7. The process according to claim 1 for preparing 3-methoxy-5-methylpyrazine-2-carboxamide, wherein 2-aminomalononitrile, or a salt thereof, is converted, using an alkali metal methoxide or alkaline earth metal methoxide and subsequent neutralization, into the aminoimidate of the formula III in which $R^2$ denotes —$C(NH)OCH_3$ and $R^3$ denotes methyl, said aminoimidate is reacted, without isolation, with methylglyoxal and, after acidification, initially converted into methyl 3-methoxy-5-methylpyrazine-2-carboxylate, and the ester function is finally amidated.

8. The process according to claim 1, wherein the reaction with an alkali metal alkoxide or alkaline earth metal alkoxide and the reaction with the glyoxal derivative is carried out at a temperature of between −30° C. and 150° C.

* * * * *